US009291692B2

(12) United States Patent
Yang et al.

(10) Patent No.: US 9,291,692 B2
(45) Date of Patent: Mar. 22, 2016

(54) BLOOD-BRAIN BARRIER RECOVERY CURVE ASSESSMENT METHOD AND SYSTEM

(71) Applicant: NATIONAL YANG-MING UNIVERSITY, Taipei (TW)

(72) Inventors: Feng-Yi Yang, Taipei (TW); I-Fang Chung, Taipei (TW); Sheng-Yao Huang, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 120 days.

(21) Appl. No.: 14/279,046

(22) Filed: May 15, 2014

(65) Prior Publication Data

US 2015/0073260 A1 Mar. 12, 2015

(30) Foreign Application Priority Data

Sep. 6, 2013 (TW) .............. 102132175 A

(51) Int. Cl.
| | |
|---|---|
| *A61B 5/055* | (2006.01) |
| *G01R 33/56* | (2006.01) |
| *A61B 5/00* | (2006.01) |
| *G01R 33/563* | (2006.01) |
| *G01R 33/48* | (2006.01) |

(52) U.S. Cl.
CPC ............ *G01R 33/5601* (2013.01); *A61B 5/055* (2013.01); *A61B 5/4064* (2013.01); *A61B 5/4839* (2013.01); *A61B 5/7285* (2013.01); *G01R 33/56308* (2013.01); *G01R 33/4814* (2013.01); *G01R 33/5635* (2013.01)

(58) Field of Classification Search
CPC .... A61B 5/055; A61B 5/4064; A61B 5/4839; A61B 5/7285; G01R 33/4814; G01R 33/5601; G01R 33/56308; G01R 33/5635
See application file for complete search history.

(56) References Cited

U.S. PATENT DOCUMENTS

| | | | |
|---|---|---|---|
| 8,275,181 B2* | 9/2012 | Muradyan | G06T 7/0012 382/128 |
| 2014/0270451 A1* | 9/2014 | Zach | A61B 5/055 382/131 |

OTHER PUBLICATIONS

Juyoung Park, et al., "The kinetics of blood brain barrier permeability and targeted doxorubicin delivery into brain induced by focused ultrasound", Journal of Controlled Release, pp. 1-9, 2012.

Paul S. Tofts, et al., "Measurement of the Blood-Brain Barrier Permeability and Leakage Space Using Dynamic MR Imaging. 1. Fundamental Concepts", Magnetic Resonance in Medicine, vol. 17, pp. 357-367, 1991.

* cited by examiner

*Primary Examiner* — Mark Remaly
(74) *Attorney, Agent, or Firm* — Muncy, Geissler, Olds & Lowe, P.C.

(57) ABSTRACT

The present invention relates to a blood-brain barrier recovery curve assessment method which uses a focused ultrasound dynamic contrast-enhanced MRI technique, in order to obtain a permeability constant of drug. Furthermore, the present invention, using a double exponential distribution function mathematical model, can estimate the actual physiological recovery curve of the blood-brain barrier. Meanwhile, the present invention also provides a monitoring system for the blood-brain barrier permeability.

14 Claims, 4 Drawing Sheets

BLOOD-BRAIN BARRIER RECOVERY CURVE ASSESSMENT METHOD AND SYSTEM

FIELD OF THE INVENTION

The present invention relates to a mathematical model for estimating the recovery time of the blood-brain barrier. In particular, it relates to a method of using mathematical model based on a double exponential distribution function to estimate the actual physiological recovery curve of the blood-brain barrier.

BACKGROUND OF THE INVENTION

The brain is a sophisticated organ. When the brain is injured, the drug is not easy to enter the brain. It is difficult to break through the bottleneck due to a special structure of brain-blood-brain barrier (abbreviated as BBB). It is a natural barrier located between blood vessels and brain, which can selectively block certain substances via the blood into the brain. Except oxygen, carbon dioxide and glucose molecules, the blood-brain barrier prevents almost any substance from entering into the brain tissue. The molecular structure of most drugs and proteins are too large, which is impossible to pass the blood-brain barrier. Although the blood-brain barrier can avoid toxic pathogens entering into the central nervous system, it also obstructs the development of therapeutic drugs for the brain.

According to the previous studies, using a focused ultrasound (FUS) with ultrasound contrast agent (UCA) to radiate in a particular area of the brain can non-invasively induce the area of the blood-brain barrier to open shortly. This allows chemotherapy drugs or antibodies with a wide range of molecular sizes to pass across the blood-brain barrier. Although the focused ultrasonic technique can significantly improve the effectiveness of drug delivery, it cannot be used to know the concentration variation when the drug releases from the blood vessels into the brain tissue. If one can predict or measure out how much drug can be transported to the target area at each time point, it will significantly enhance the potential impact of drug delivery on the ultrasound-induced blood-brain barrier opening in the brain.

In order to predict how much drug will be transported to the brain, it requires to find the permeability of the blood-brain barrier. It is known that dynamic contrast-enhanced MRI (DCE-MRI) through signal intensity changes of DEC-MRI contrast agent can be used to monitor the vascular permeability changes when opening the blood-brain barrier over time. In addition, using the pharmacokinetic model proposed by Tofts and Kermode in 1991 (see Magn.625 Reson. Med. 17 (2) (1991) 357-367) can estimate the permeability of the MRI contrast agent. Park et al. applied the theory to propose a mathematical model to estimate the recovery period of the blood-brain barrier $K_{trans}(t)=K_{trans}^{0} \times \exp(-t/R)$ (please refer to Journal of Controlled Release 2012 Aug. 20; 162 (1):134-42). In Park's model, it only considers the permeability changes of the ultrasonic irradiation area (half brain), for estimating the length of time to open and close the blood-brain barrier through the half-life. However, for future applications, if it only assesses the decay rate of the target area, it might be inadequate. After all, the impact of decay rate is affected by the differences between individuals. Thus, if it does not consider the difference as a control, it cannot clearly point out the closing time of the blood-brain barrier.

SUMMARY OF THE INVENTION

Based on the consideration of the disadvantages mentioned above, the present invention provides an assessment method and system for the blood-brain barrier recovery curve. Using the calculated permeability constant of the left and right brain and a double exponential distribution function can establish a mathematical model, which is able to estimate the recovery time for opening and closing the blood-brain barrier, using the true blood-brain barrier of the recovery curve.

Accordingly, in one aspect, the present invention provides an assessment method for the blood-brain barrier recovery curve, comprising the steps of: providing an ultrasonic contrast agent to a subject; introducing ultrasound in the subject's brain target area in order to open the blood-brain barrier; providing a dynamic contrast-enhanced MRI (DCE-MRI) contrast agent to the subject after applying ultrasound; imaging the whole brain with DCE-MRI; obtaining DCR-MRI imaging signal of the brain tissue permeability on the target area and the non-target area at different time points after inducing DCE-MRI contrast agent; using the general kinetic model (GKM) to calculate permeability constant $K_{trans}$ at different time points and calculate the permeability constant $K_{trans}$ decay rate by using a permeability constant $K_{trans}$ equation:

$$K_{trans}(t) = K_{trans}^{sonication} \times \exp(-a \times t) + K_{trans}^{non-sonication} \times \exp(-b \times t),$$

and to obtain a blood-brain barrier recovery curve;
wherein, the $K_{trans}(t)$ is the permeability constant of the drug at time t in the target area;
$K_{trans}^{sonication}$ is the permeability constant of the drug at time t=0 in the target area;
$K_{trans}^{non-sonication}$ is the permeability constant of the drug at time t=0 in the non-target area.
Values a and b are parameters estimated from curves.

In one embodiment of the present invention, the target area means either left or right half-brain of the subject's brain, and the non-target area is the other half of the subject's brain. The permeability constant $K_{trans}$ in the kinetic model is calculated from the concentration changes of the DCE-MRI contrast agent in the brain.

In another specific embodiment of the present invention, it uses the parameters a, b of the exponential function as a recession function of permeability constant $K_{trans}$. Then it uses Matlab curve estimation method to obtain the parameters of the exponential distribution function, named as the decay rate of the permeability constant $K_{trans}$. The values a and b in the equation are estimated by the calculated by the calculated $K_{trans}$ value at different time points, and a Matlab's optimal curve estimation method (Levenberg-Marquardt algorithm). Wherein, a>0, b<0, and t<72 h in the equation. The permeability state of the target area has been restored to the same degree of the non-target area when the physiological recovery curve of the blood-brain barrier falls within the mean value and half a standard deviation of permeability constants obtained from the non-target areas.

In a preferred embodiment of the present invention, at least one set of DCE-MRI cerebral angiography images are obtained after applying ultrasound and before injecting the DCE-MRI contrast agent.

On the other hand, the present invention provides a monitoring system for the permeability of the blood-brain barrier to estimate the recovery curve of the blood-brain barrier. The system includes: an ultrasonication device for transmitting an ultrasonic signal to a target area of a subject's brain, thereby opening the blood-brain barrier of the target area; a dynamic contrast-enhanced MRI (DCE-MRI) device for creating whole brain imaging of the subject, which is used to obtain DCE-MRI image signals showing the brain tissue permeability in the target area and the non-target area at different time points; and an operation processing device, which includes an operating program for the operation processing of the image signals received by the DCE-MRI, and further estimating the recovery curve of the blood-brain. Wherein the operating program performs the following steps: using a general kinetic model (GKM) to calculate the received image signal of DCE-MRI to obtain the permeability constant $K_{trans}$ at different time points; using the following equation to calculate the decay rate of the permeability constant $K_{trans}$: $K_{trans}(t)=K_{trans}^{sonication}\times\exp(-a\times t)+K_{trans}^{non-sonication}\times\exp(-b\times t)$; and estimating the declining rate of the permeability constant $K_{trans}$ by the recovery curve of the blood-brain barrier. Wherein the $K_{trans}(t)$ is the permeability constant of the drug at time t in the target area; $K_{trans}^{sonication}$ is the permeability constant of the drug at time t=0 in the target area; $K_{trans}^{non-sonication}$ is the permeability constant of the drug at time t=0 in the non-target area; and values a and b are estimated parameters derived from recovery curve.

In one embodiment of the present invention, the ultrasonic device is a pulse focused ultrasound system with an ultrasonic probe device of single piezoelectric crystal having anti-magnetic properties.

In the specific embodiment of the present invention, the monitoring system further includes a three-dimensional positioning system, which is made of insulating material, for mounting on an ultrasound probe. The system has a positioning arm to adjust the position of the ultrasound probe. The positioning system is made of the acrylic material, and the positioning arm is made of bakelite.

In another specific embodiment of the present invention, the system further includes an injection device. The injection device is set up outside MRI room and connected with a connecting tube connected to the subject, in order to inject the medicine outside MRI room. Thus, when the drug enters into the body, the whole permeation process can be monitored in the brain tissue.

The present invention provides the assessment method and system for the recovery curve of the blood-brain barrier. Through the calculation of the drug permeability constant and situation on the lesion area of the left and right half brain, it shows differences between the experimental group (the target area) and the control group (the non-target areas) for using the mutual relationship of two sets of experiments, thereby accurately estimating the state to recover the blood-brain barrier, obtaining the physiological recovery curve of the blood-brain barrier, and then estimating the recovery time. The proposed mathematical model in the present invention, due to the elimination of individual differences on the curve, can clearly point out the BBB-off time. In practical applications, it can be used to control the quantitative relationship of the drug's permeability into the lesions. Thus, within the effective time entering into the lesion area, the dose can attain the medical effect.

DETAILED DESCRIPTION OF THE INVENTION

The other characteristics and advantages of the present invention will be further illustrated and described in the following examples. The examples described herein are using for illustrations, not for limitations of the invention.

Figure 1:
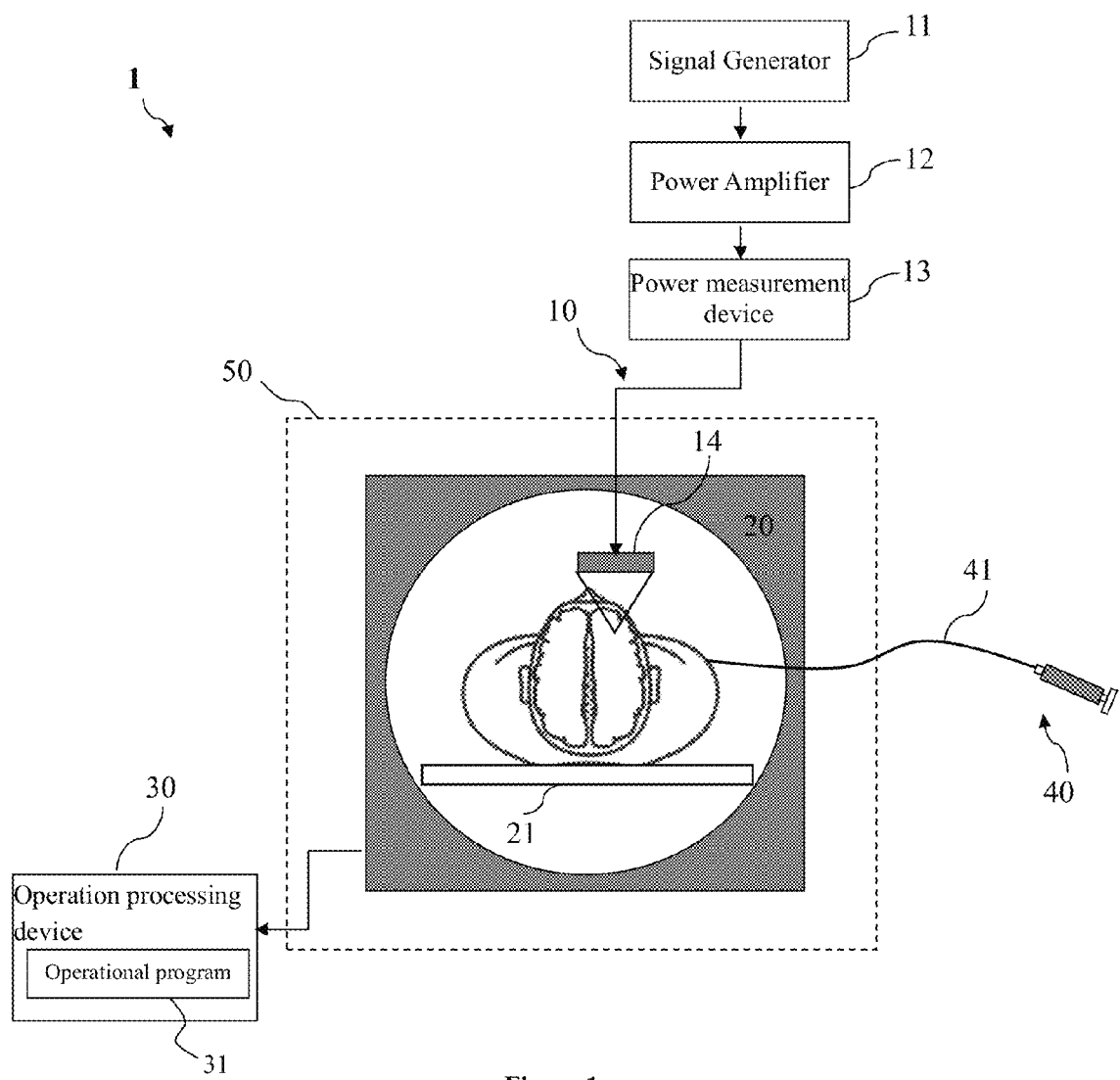
FIG. 1 shows that the present invention has a preferred embodiment of the blood-brain barrier permeability control system.

Please refer to FIG. 1—the monitor system of the blood-brain barrier permeability in the present invention. The system 1 is comprised of an ultrasonic device 10, a dynamic contrast-enhanced MRI (DCE-MRI) device 20, an operation processing device 30, and an injection device 40. The ultrasonic device 10 and the dynamic contrast-enhanced magnetic resonance imaging apparatus 20 is disposed inside MR imaging chamber 50, and the operation processing device 30 and the injection device 40 is disposed outside the MR imaging chamber 50.

The present invention relates to the use of the focused ultrasound (FUS). The ultrasonic device 10 includes a signal generator 11, an amplifier 12, a power measurement device 13, and an ultrasonic probe 14, for transmitting an ultrasonic signal to the target area of the subject's brain, thereby opening the target area of the blood-brain barrier. The dynamic contrast-enhanced magnetic resonance imaging apparatus 20 is used for the whole brain imaging, in order to obtain DCE-MRI video signals for the brain permeability at different time points. Later, send the image signal acquired by DCE-MRI 20 to the operation processing device 30 for data analysis and processing, in order to estimate the blood-brain barrier to physiological recovery curve.

In order to make the ultrasound probe 14 work properly inside the DEC-MRI, in an embodiment of the present invention, it selects a single element PZT of the focused ultrasonic probe (H-101, SONIC CONCEPTS, INC), mainly because the probe 14 possesses MRI compatible properties, which are not subject to magnetic interference for controlling the output of the ultrasound. The front of the probe 14 piezoelectric crystal is installed with a conical acrylic container, which is filled with degassed water inside as a medium to help sonic wave conduction. Meanwhile, both polyurethane film and the black O-ring are used to seal the top of the circular cone gap. The steps complete the encapsulation of the probe 14.

In one embodiment of the present invention, the system is further comprised of a stereotaxic apparatus (not shown) for setting up the ultrasound probe 14. The stereotaxic apparatus has a positioning arm, which is adjustable to move the ultrasound probe 14, and provides a solid support. The conventional stereotaxic instrument is made of metal and cannot be placed into the MRI scanning instrument. In order to solve this problem, in another embodiment of the present invention, the stereotaxic instrument is developed to be made of an insulating material; preferably, the stereotaxic instrument system is made of acrylic material, and the positioning arm is made of bakelite. When the ultrasound probe 14 is mounted on a stereotaxic apparatus after accurate positioning, the stereotaxic instrument can be placed directly inside MRI chamber 50 near the angiographic hole of the magnet center, and then execute the work for the magnetic resonance imaging.

Figure 2:
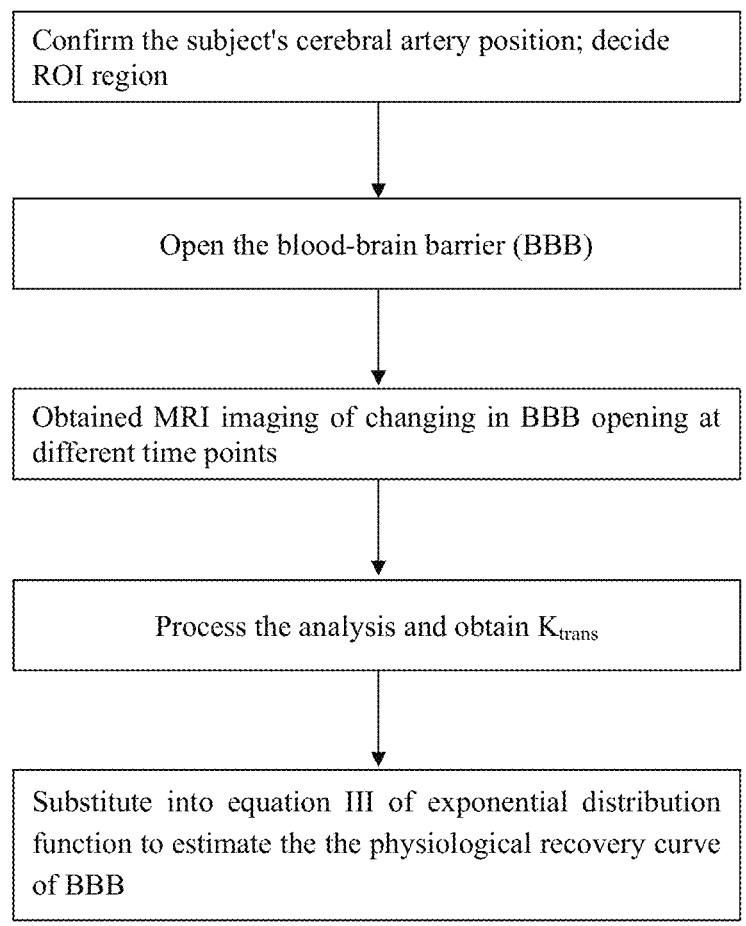
FIG. 2 shows that the present invention has a preferred embodiment of the blood-brain barrier to estimate the recovery curve.

Please refer to FIG. 2, which is the blood-brain barrier recovery curve flow diagram for estimation in the present invention. Firstly, use DCE-MRI 20 to confirm the cerebral artery position of the subject. Next, select the region of interest (ROI). Then, use the focused ultrasound to open the blood-brain barrier and use DCE-MRI 20 to take the whole brain imaging of the subject. Obtain the brain tissue permeability of DCE-MRI image signal at different time points on applying the ultrasound on the target and the non-target area. Finally, send the image obtained by DCE-MRI 20 to the operation processing device 30, via computing program 31 to estimate the blood-brain recovery curve. The computing program 31 takes advantage of general kinetic model (GKM) proposed by Tofts to calculate permeability constant. Furthermore, use the proposed mathematical model to estimate the blood-brain barrier physiological recovery curve of the subject. Detailed curve estimation process will be illustrated with the following specific embodiment for further explanation.

Step a. Confirm ROI region. The present invention is primarily designed for four experimental conditions with different time points (the use of four rats for each experiment). Rats are anesthetized and fixed on the table 21. Firstly, use DCE-MRI imaging to obtain a set of 3D TOF-MRA images (Time-of-Flight magnetic resonance angiography), in order to observe the position of middle cerebral artery in the rat's brain (MCA) and then determine the subsequent image processing of ROI area. Imaging specifications of DCE-MRI are as follows: TR/TE=14/5.42 ms; Flip angle=200; Slice thickness=0.3 mm; FOV=85×85 mm2; matrix=256×256; Slab=5; Scanning time=10 min 27 s.

Step b. Open the blood-brain barrier. Through ultrasound contrast agent (UCA), irradiate with ultrasound in the target area to open the blood-brain barrier of the target area. One particular embodiment of the present invention uses microbubbles as the ultrasonic contrast agent to irradiate the right brain of the normal rat (the target area) with the focused ultrasonic pulse to open the brain's blood-brain barrier. The micro-bubble contrast agent can be selected from any of the following matters: ALBUNEX®, SONOZOID®, SONOVUE®, SONOVIST®, OPTISON®, LEVOVIST® or DEFINITY®. The embodiment choose SonoVue (Bracco International, Amsterdam, The Netherlands) dry powder contrast agent. The dry powder is first added to a saline solution for the preparation of sulfur hexafluoride (SF6) microbubble suspension contrast agent. The average diameter is 2.5 μm, and the concentration is 1~5×10$^8$ bubbles/ml. In safety studies, the saline solution is considered as no difference. The parameters of the focused ultrasound pulse are set as follows: Burst Length is 50 (ms); the duty cycle is 5%; the pulse repetition frequency (PRF) is 1 Hz; and ultra-sonic irradiation time is 60 (s); the acoustic power is fixed at 3.41 (W). Experimentally, use 1 cc syringes to extract ultrasound contrast agent mixed with saline. Then inject via the injection device 40 to the rat's tail vein, and wait 15 seconds until ultrasound contrast agent starts circulating the whole body with the blood. Then irradiate the rats with the focused ultrasound.

Step c. Confirm background signals. Before injection of MRI contrast agent, it requires to obtain at least one set of DCE-MRI cerebral angiography imaging, which is the initial state of brain imaging, as a background signal. In this embodiment, two sets of scanning images take about 3 minutes for the whole scanning process.

Step d. Obtain DCE-MRI imaging signals for the brain tissue permeability at different time points. Before scanning the MRI images of the third group, two sets of images in four experimental groups were scanned and obtained at 0, 15, 25, 120 min via the intravenous injection of MRI contrast agent. In the embodiments, the contrast agent used in MRI is Gd-DTPA-BMA (Gadodiamide, Omniscan), at a dose of 1 mmol/kg. The scanning process took about one hour for 38 groups of DCE-MRI scanning continuously. Heretofore, the mode of administration is known. Firstly, inject the contrast agent externally and the rats were positioned on the platform. Then the rats were sent into the MRI. The drugs begun to work when the rats were sent into MRI. However, MRI imaging cannot monitor the changes in the initial concentration of the drug. When MRI scanning begins, most of the drugs is metabolized. Thus, the experimental data obtained will produce distortion. In view of the disadvantages of the known technique without the real-time monitoring, in the system 1 of the present invention, the injection apparatus 40 further includes a connection tube 41 to the catheter on the rat's tail vein (the connection tube 41 used in this experiment tube is PE-50 hose). The injection device 40 of the present invention is disposed outside the magnetic resonance chamber 50. Thus, after the rats are sent into MRI, inject Gd-DTPA-BMA contrast agent into the rats via the connection tube 41 in the magnetic resonance chamber 50. Therefore, when the drug enters into the body, the drug permeating in the brain tissue can be monitored. At the same time, through the injection device 40 of the present invention, repetition can be achieved.

In step c, d, 40 groups of T1 DCE-MRI scan were conducted to observe the changes in the blood-brain barrier of the rat's brain before and after ultrasonic irradiation at different time points. The parameters of each T1 DCE-MRI are set as follows: number of slices=22 (covering the entire brain to detect the opening region of the blood-brain barrier); TR/TE=500/13 ms; FOV=47×80 mm2; matrix=152×256 pixels; Slice thickness=1.5 mm; Scanning time=97 s.

Step e. MRI image processing. Use Matlab to detect and select the above 40 DCE-MRI images at different time points from each rat, in order to obtain average signals of the blood-brain barrier's opening region. All the mice are under the same parameters of the focused ultrasound, for obtaining the signals from the vascular region and the BBB opening region. Use it as an average signal of the parameters of the ultrasound.

In this embodiment, according to the theory of Tofts-Kermode, the ROI of rat is defined as two chambers having two compartment volume for a blood (plasma) space and an extravascular extracellular space (EES). The concentration of t Gd-DTPA-BMA contrast agent can be calculated by the conversion of the average signal under the ultrasonic parameters using equation I.

$$C_{Gd} = \frac{S_{post} - S_{pre}}{S_{pre} \times R_{10} \times r_1} \quad (I)$$

Wherein, $C_{Gd}$ is the contrast agent concentration; $S_{pre}$ the average signal strength before the injection of contrast agent; $S_{post}$ the average signal strength after the injection of contrast agent; $T_{10}$ is the baseline (i.e., before the injection of contrast agent) longitudinal relaxation time. In this experiment, $T_{10}$ values of the blood and the brain are set 1.5 s and 0.9 s, respectively; $r_1$ is the corresponding longitudinal relaxation, i.e. increase in the relaxation rate per unit; $r_1$ of experiments is set to 4.62 mM$^{-1}$ s$^{-1}$.

Next, substitute CGd into the formula II in order to obtain the parameters of the two permeability coefficient $K_{trans}$ and $K_{ep}$, respectively.

$$C_t(t) = \left(\frac{K_{trans}A_1}{m_1 - K_{ep}} + \frac{K_{trans}A_2}{m_2 - K_{ep}}\right)e^{-K_{ep}t} - \left(\frac{K_{trans}A_1}{m_1 - K_{ep}}\right)e^{-m_1 t} - \left(\frac{K_{trans}A_2}{m_2 - K_{ep}}\right)e^{-m_2 t} \quad (II)$$

Wherein, $C_t(t)$ is the relationship of the contrast agent concentration changing along the time in the experiment; $K_{trans}$ (min$^{-1}$) is the volume transfer constant, which means the rate constant of the contrast agent permeating from the blood (plasma) to EES (i.e. microvascular endothelial permeability rate P and the surface S; the product: P*S); $K_{ep}$ (min$^{-1}$) is the rate constant, which means the rate constant of space as the contrast agent returns from the EES blood (plasma); A1, A2 are the blood concentration of the initial values; $m_1$, $m_2$ are the changing rate of the blood concentration.

All of the above weighted images of T1 DCE-MRI data were analyzed and processed in Matlab.

Figure 3:
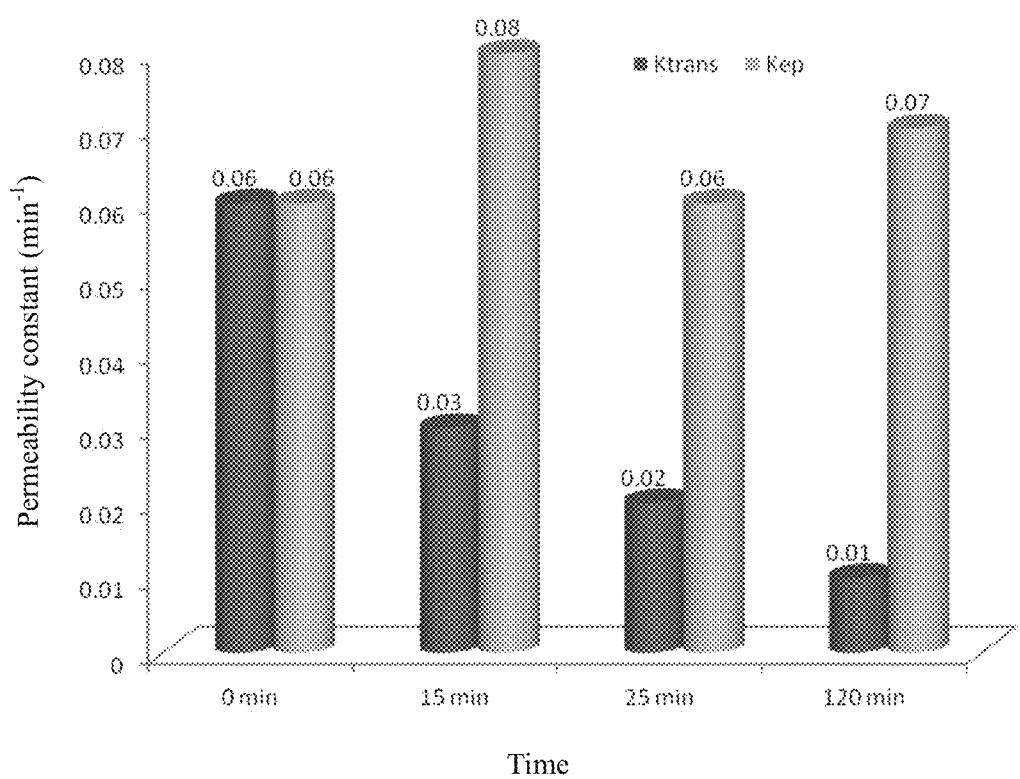
FIG. 3 is based on one embodiment of the present invention to estimate the brain penetration constant at different time points.

Please refer to FIG. 3, according to the aforementioned method, proposed by Tofts-Kermode, with Matlab optimal curve estimation method Levenberg-Marquardt fitting algorithm (Matlab R2008b, MathWorks, Inc., Natick, Mass., USA), the permeability constant $K_{trans}$ of the dynamic model can be further found. Use this method to estimate the permeation constant values $K_{trans}$=0.06, 0.03, 0.02, 0.01 in the right brain at t=0 min, 15 min, 25 min, 120 min, respectively.

The $K_{trans}$ value were obtained at different time points. Then substitute the values into the formula III exponential distribution function:

$$K_{trans}(t) = K_{trans}^{sonication} \times \exp(-a \times t) + K_{trans}^{non\text{-}sonication} \times \exp(-b \times t) \qquad (III)$$

Wherein, $K_{trans}(t)$ is the permeability constant of the drug in the target area (right brain) at time of t; $K_{trans}^{sonication}$ is the permeability constant of drug in the target area at t=0 after ultrasonic irradiation; $K_{trans}^{non\text{-}sonication}$ is the permeability constant of drug in the non-target area (left brain) at t=0 without ultrasonic irradiation. Values a and b are estimated parameters derived from recovery curve. The parameters of an exponential function can be a recession function of permeability constant $K_{trans}$. Re-use of Matlab optimal curve estimation method to obtain the parameters on the exponential distribution function, named as permeability constant $K_{trans}$ decay rate. In the proposed mathematical model of the invention, a>0, b<0, and t<72 hrs, if t>72 hrs, this mathematical model $K_{trans}(t)$ is only needed to consider $K_{trans}^{non\text{-}sonication}$, i.e. the permeability constant of the unirradiated left brain area. Without estimating the changes in permeability constant, it will affect the health of the individual experiments and generate the errors of the estimation, mainly due to long ultrasound exposure In one embodiment of the present invention, a=4.006 (0.5794, 7.432), b=−0.1119 (−1.328, 1.104), has 95% confidence interval.

In addition, in the experiment, calculate the average value of the permeability constant at four point of time (Mean=0.008) and standard deviation (Std), as experimental control. Through the confidence interval, define a one-half standard deviation range, as the ranges of the blood-brain barrier recovery period in the experiment.

Figure 4:
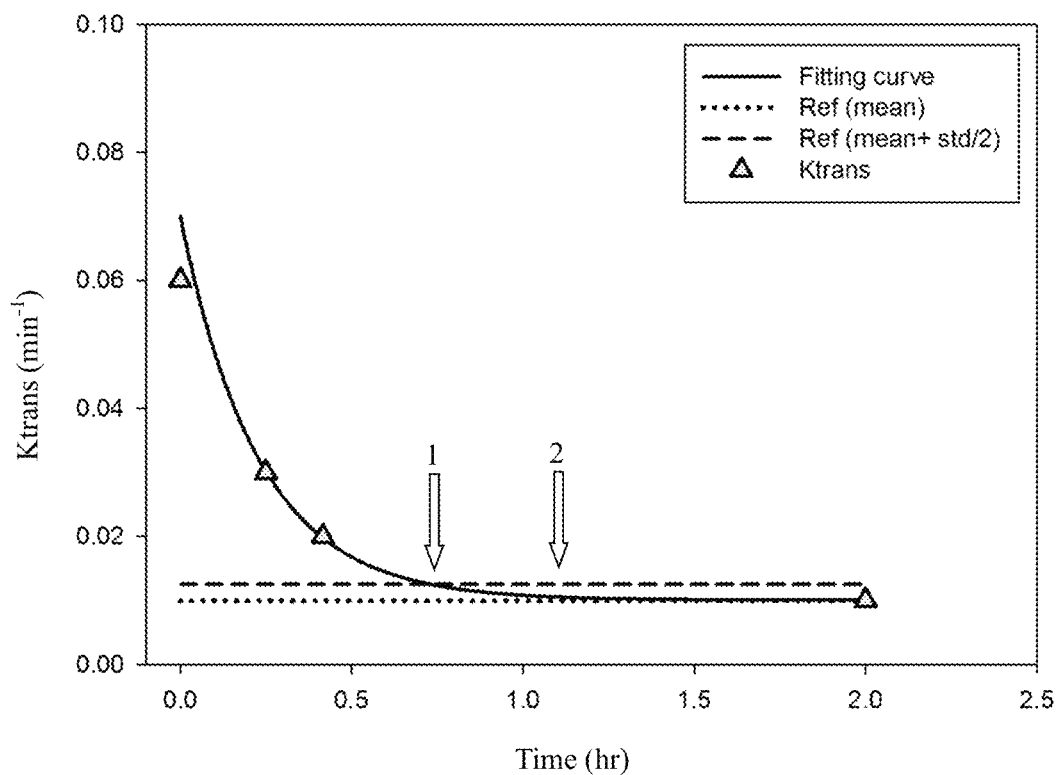
FIG. 4 is based on one embodiment of the present invention to estimate the physiological blood-brain barrier recovery curve.

Please refer to FIG. 4, which is the diagram of the blood-brain barrier physiological recovery curve estimation using the present invention. According to the proposed mathematical model of the present invention, calculate the permeability constant in the aforementioned experimental values via Matlab for the non-linear estimation of the curve graph. The solid line in the figure (-) is generated through Matlab to estimate the blood-brain barrier recovery curve; the dotted line ( . . . ), as the control group, is the average permeability constant of un-irradiated brain tissue in the left brain; the dashed line ( - - - ) is the average permeability constant plus one-half standard deviation value of un-irradiated brain tissue in the left brain; Arrow 1 to arrow 2 means the range of the blood-brain barrier recovery time. When the blood-brain barrier physiological recovery curve falls within the average value and half a standard deviation, it means that the blood-brain barrier has been recovered to the same permeability state as the left-brain; in other words, it is back to the non-irradiated pre-osmosis.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of assessing the blood-brain barrier recovery curve, comprising:
   providing an ultrasound contrast agent to a subject;
   applying an ultrasound to a brain target area of the subject to open the blood-brain barrier;
   applying the ultrasound to the brain target area of the subject at different time points with a dynamic contrast-enhanced MRI (DCE-MRI);
   using DCE-MRI for the whole brain imaging to obtain DCE-MRI image signals of brain permeability on the target and non-target area at different time points;
   analyzing the obtained DCE-MRI image signals and using general kinetic model (GKM) to calculate the permeability constant $K_{trans}$ at different time points; and
   calculating the permeability constant $K_{trans}$ decay rate by using a permeability constant $K_{trans}$ equation (III):

$$K_{trans}(t) = K_{trans}^{sonication} \times \exp(-a \times t) + K_{trans}^{non\text{-}sonication} \times \exp(-b \times t) \qquad (III)$$

and to obtain a blood-brain barrier recovery curve;
   wherein, the $K_{trans}(t)$ is the permeability constant of the drug in the target area at time of t; $K_{trans}^{sonication}$ is the permeability constant of drug in the target area at t=0 after ultrasonic irradiation; $K_{trans}^{non\text{-}sonication}$ is the permeability constant of drug in the non-target area at t=0 without ultrasonic irradiation; and the values a and b are estimated parameters derived from the recovery curve.

2. The method of claim 1, wherein the target area for the subjects is either the left or right half brain, and the non-target area is the other half brain of the subject.

3. The method of claim 1, wherein the permeability constant $K_{trans}$ in the dynamic model is obtained by the concentration density changes of DCE-MRI contrast agent in the brain tissue region.

4. The method of claim 1, wherein the values a and b in the equation (III) are estimated by the calculated $K_{trans}$ value at different time points and a Matlab's optimal curve estimation method (Levenberg-Marquardt algorithm).

5. The method of claim 1, wherein the criteria of the equation (III) is: a>0, b<0, and t<72 h.

6. The method of claim 1, wherein the permeability state of the target area has been restored to the same degree of the non-target area when the blood-brain barrier recovery physiological curve falls within the mean value and half the standard deviation of permeability constants obtained from the non-target area.

7. The method of claim 1, wherein at least one set of DCE-MRI cerebral angiography images are obtained after applying ultrasound and before injecting the DCE-MRI contrast agent as a background signal.

8. A system of monitoring blood-brain barrier permeability to estimate the recovery curve of blood-brain barrier, comprising:
an ultrasonication device to transmit an ultrasonic signal in a target area of a subjects' brain, thereby opening the blood-brain barrier of the target area;
a dynamic contrast-enhanced MRI (DCE-MRI) device for creating whole brain imaging of the subject, which is used to obtain DCE-MRI image signals showing the brain tissue permeability in the target area and non-target area at different time points; and
an operation processing device, which includes an operating program for the operation processing of the image signals received by the DCE-MRI to estimate the blood-brain recovery curve; wherein the operating program performs the following steps:
using a general kinetic model (GKM) to calculate received DCE-MRI image signals to obtain $K_{trans}$ at different time points;
using formula (III) to calculate $K_{trans}$ decay rate:

$$K_{trans}(t) = K_{trans}^{sonication} \times \exp(-a \times t) + K_{trans}^{non\text{-}sonication} \times \exp(-b \times t) \quad (III);$$

wherein the $K_{trans}(t)$ is the permeability constant of the drug in the target area at time of t; $K_{trans}^{sonication}$ is the permeability constant of drug in the target area at t=0 after ultrasonic irradiation; $K_{trans}^{sonication}$ is the permeability constant of drug in the non-target area at t=0 without ultrasonic irradiation, and values a and b are estimated parameters derived from recovery curve; and
estimating the decay rate of the permeability constant $K_{trans}$ by the recovery curve of the blood-brain barrier.

9. The system of claim 8, wherein the ultrasonication device is a pulse focused ultrasound system with a ultrasound probe of single piezoelectric crystal having anti-magnetic properties.

10. The system of claim 8, wherein the calculating step of $K_{trans}$ at different time points further comprising an estimation step of values a and b in the equation (III) by using Matlab's optimal curve estimation method (Levenberg-Marquardt algorithm) on the $K_{trans}$ at different time points.

11. The system of claim 8, wherein the calculating step of $K_{trans}$ comprises a step of calculating the concentration changes of the DCE-MRI contrast agent in the brain to obtain $K_{trans}$ at different time points.

12. The system of claim 8, wherein the system further comprises a stereo positioning apparatus made of an insulation material, on which is set up an ultrasound probe and equipped with a positioning arm for the position adjustment of the ultrasound probe.

13. The system of claim 12, wherein the positioning system is made of an acrylic material, and the positioning arm is made of a bakelite material.

14. The system of claim 8, wherein the system further comprises a injection device, which is disposed outside the magnetic resonance chamber and equipped with a connecting tube connected to a subject inside the magnetic resonance chamber.

\* \* \* \* \*